(12) United States Patent
VanEperen et al.

(10) Patent No.: US 7,179,343 B2
(45) Date of Patent: Feb. 20, 2007

(54) METHOD FOR BONDING SURFACES ON A WEB

(75) Inventors: David J. VanEperen, Appleton, WI (US); Joseph D. Coenen, Kaukauna, WI (US); Jack L. Couillard, Menasha, WI (US); Walter A. Mattingly, Appleton, WI (US); Robert L. Popp, Hortonville, WI (US); Heather S. Mortell, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 536 days.

(21) Appl. No.: 10/741,043

(22) Filed: Dec. 19, 2003

(65) Prior Publication Data

US 2005/0133150 A1  Jun. 23, 2005

(51) Int. Cl.
*A61F 13/15* (2006.01)
*B32B 37/16* (2006.01)

(52) U.S. Cl. .................. 156/163; 156/164; 156/229; 156/494; 156/495; 156/496

(58) Field of Classification Search ............... 156/163, 156/164, 229, 494, 495, 496
See application file for complete search history.

(56) References Cited

U.S. PATENT DOCUMENTS

| 4,240,866 A | 12/1980 | Rega |
| 4,285,747 A | 8/1981 | Rega |
| 4,293,367 A | 10/1981 | Klasek et al. |
| 4,397,704 A | 8/1983 | Frick |
| 4,578,133 A | 3/1986 | Oshefsky et al. |
| 4,610,751 A | 9/1986 | Eschler |
| 4,617,082 A | 10/1986 | Oshefsky et al. |
| 4,801,345 A | 1/1989 | Dussaud et al. |
| 4,915,767 A | 4/1990 | Rajala et al. |
| 4,917,746 A | 4/1990 | Kons et al. |
| 4,940,464 A | 7/1990 | Van Gompel et al. |
| 4,941,939 A * | 7/1990 | Nomura et al. ............ 156/495 |
| 4,968,313 A | 11/1990 | Sabee |
| 5,091,039 A | 2/1992 | Ujimoto et al. |
| 5,275,676 A | 1/1994 | Rooyakkers et al. |
| 5,556,504 A | 9/1996 | Rajala et al. |
| 5,716,478 A | 2/1998 | Boothe et al. |
| 5,759,340 A | 6/1998 | Boothe et al. |
| 6,375,769 B1 * | 4/2002 | Quereshi et al. ............ 156/229 |
| 6,440,246 B1 * | 8/2002 | Vogt et al. ................ 156/163 |

(Continued)

FOREIGN PATENT DOCUMENTS

| EP | 0 047 106 B1 | 10/1984 |
| WO | WO 01/17473 A1 | 3/2001 |
| WO | WO 03/028607 A2 | 4/2003 |

*Primary Examiner*—Jeff H. Aftergut
(74) *Attorney, Agent, or Firm*—John L. Brodersen; Randall W. Fieldhack

(57) ABSTRACT

A method for bonding a strip, such as a leg elastic or the like, to an opening on a web of material. The method includes providing a web that includes at least one opening and defines at least a first bonding surface adjacent each opening. For each opening the method includes: deforming the web to modify the shape of the opening, providing a strip defining a second bonding surface, bonding together at least portions of the first and second bonding surfaces of the modified opening and relaxing the web.

38 Claims, 10 Drawing Sheets

U.S. PATENT DOCUMENTS

| | | |
|---|---|---|
| 6,482,195 B1 | 11/2002 | Kumasaka |
| 6,533,879 B2 | 3/2003 | Quereshi et al. |
| 6,540,857 B1 | 4/2003 | Coenen et al. |
| 6,645,190 B1 | 11/2003 | Olson et al. |
| 2003/0114826 A1 | 6/2003 | Roessler |
| 2003/0217803 A1 | 11/2003 | Hermansson |

* cited by examiner

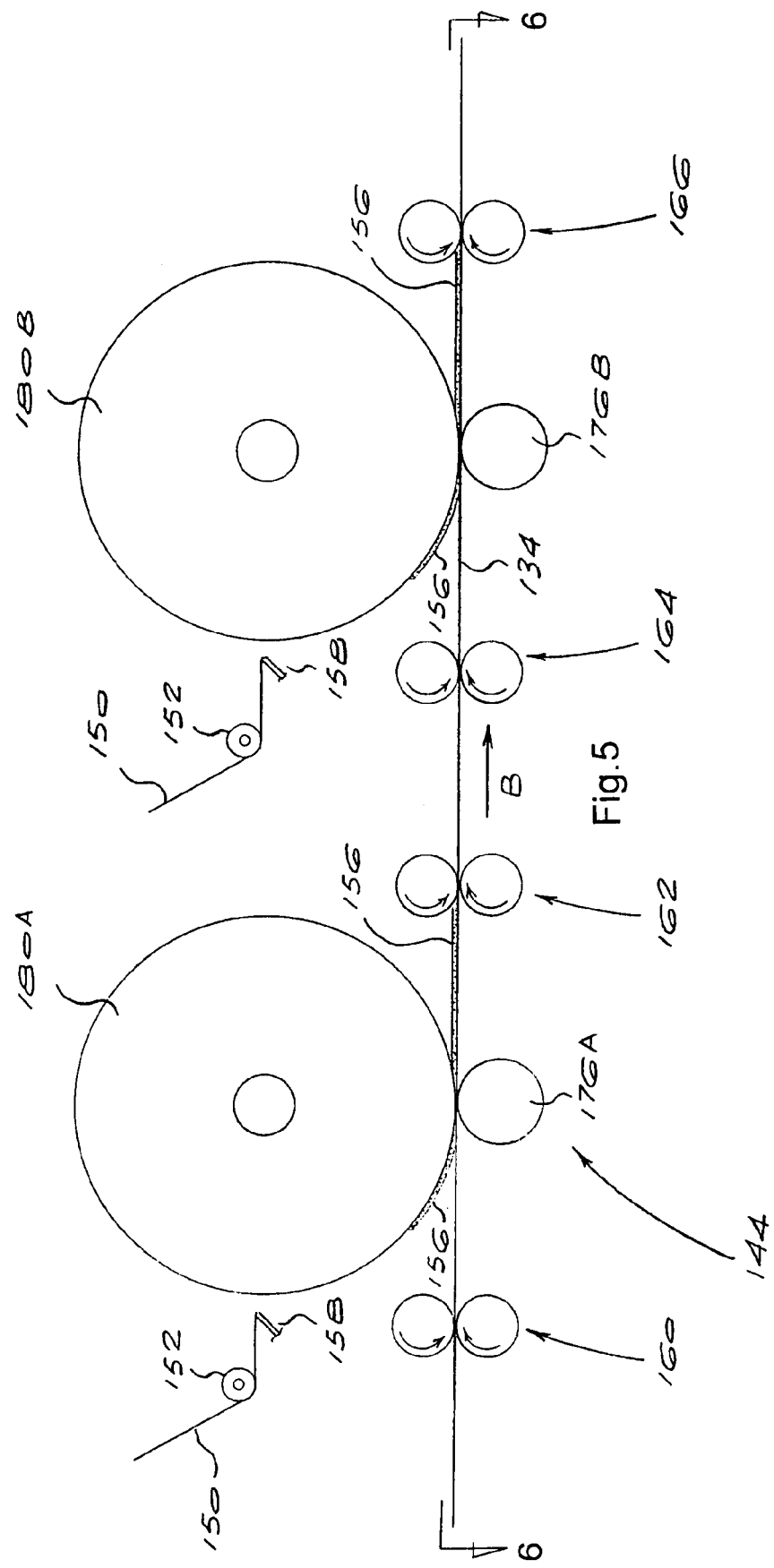

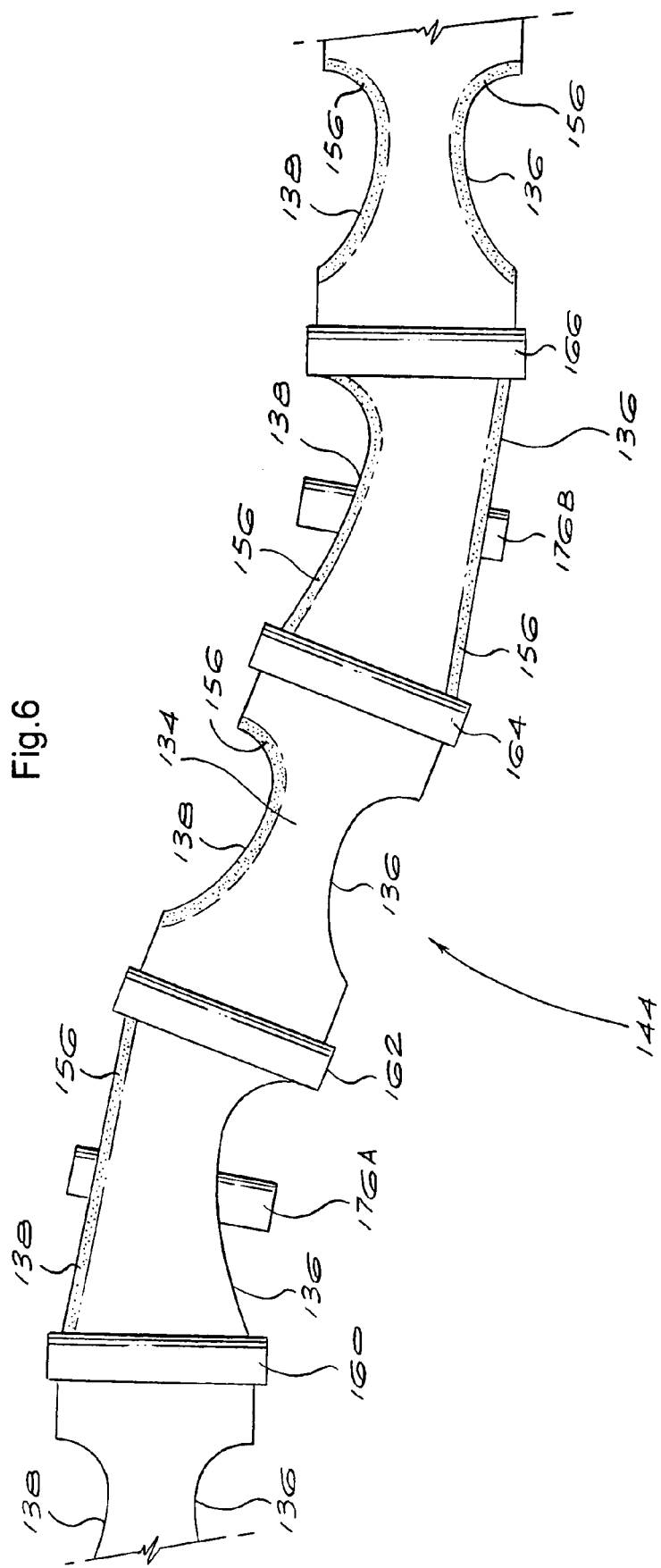

METHOD FOR BONDING SURFACES ON A WEB

FIELD OF THE INVENTION

The present invention relates to the bonding of surfaces on a moving web. More specifically, the invention relates to a method for bonding strips, such as leg elastics and the like, to curved edge regions of a moving web to form leg openings for a pant-like garment.

BACKGROUND OF THE INVENTION

Absorbent products such as diapers, training pants, adult incontinence garments, and the like generally are formed from a liquid pervious bodyside liner, a liquid impervious outer cover, and an absorbent assembly sandwiched between the bodyside liner and the outer cover. Typically, these garments include a pair of leg openings having elasticised portions which are designed to form a snug fit around a wearer's legs to prevent leakage from the garment.

Various different methods for attaching leg elastics to a moving web so as to provide elasticised leg openings on the web are known. For example, elastic ribbons may be applied along a straight line to a moving web by continuously running the elastic and the web at relatively high speeds while adhesive is applied to the elastic, and then bringing the elastic and the web together so that the elastic is bonded to the web to form elasticised portions on the web.

Although straight leg elastics improve the fit of leg openings in a garment, considerably better results can be obtained if the elastic is curved or contoured to follow the general curvature of the thigh or crotch area of a wearer. Methods for applying curved leg elastics to a moving web are also known. For example, in one method, an elastic ribbon is rolled directly into engagement with a moving web by a nip roll, and an oscillating roll is provided for oscillating the elastic ribbon so that the ribbon is applied to the nip roll in a curved line path for application to the moving web in the curved line path. In another method, a rotatable roll is moved in a direction transverse to the direction of a moving web, and the movement of the roll is imparted to an elastic ribbon which subsequently is adhered to the moving web.

A drawback with methods in which an elastic ribbon is applied continuously to a moving web is that the application of leg elastics is not limited to those regions of the web which are intended to form leg openings. As a result, various attempts have been made to apply discrete, curvilinear elastic strips to a moving web. In one method, elastic strips are adhered to flexible strip supports carried by transfer members on a rotatable support while the strip supports are in a linear configuration. The configuration of the strip supports and the elastic strips is then changed to a desired curvilinear configuration, and the transfer members are brought into transfer contact with the moving web to transfer the curvilinear elastic strips to the web. In another method, an elastic strip is stretched and wrapped about a curved side of a puck, and the puck is then rotated into alignment with a moving web to transfer the curved elastic strip, in a stretched condition, to the moving web, thereby forming a curved leg elastic on the web. The webs in these methods usually move at high linear speeds, often in excess of 600 feet per minute, and as the degree of curvature of the leg elastic increases, so the difficulty of holding and shaping the leg elastic, and of bonding the leg elastic at high speeds to the web, increases. Also, sharp direction changes of the applied strips tend to set up relatively high mechanical stresses in the moving web, and these stresses can damage the web material.

Accordingly, there remains a need in the art for a method which facilitates high-speed application of discrete, curved leg elastics or the like to curved leg openings on a moving web when forming elasticised leg openings on the web. There is also a need for a method of bonding discrete, curved leg elastics to a moving web without inducing relatively high mechanical stresses in the web.

SUMMARY OF THE INVENTION

The present invention is directed to a method for applying a strip, such as a discrete, curved leg elastic or the like, to a curved leg opening on a moving web for forming a leg portion on a pant-like absorbent garment. Accordingly, in a first aspect of the invention, there is provided a method for bonding surfaces on a web including providing a web which includes leg openings and which defines at least a first bonding surface adjacent each leg opening. For each leg opening, the process includes i) deforming the web so as to modify the shape of the leg opening, ii) providing a strip defining a second bonding surface, iii) bonding together at least portions of the first and second bonding surfaces adjacent the modified leg opening, and iv) relaxing the web.

In another aspect, the invention is directed to a method for bonding surfaces on a moving web including providing a web which has curved leg openings and which defines at least a first bonding surface adjacent each leg opening. The method also includes, for each leg opening, deforming the web so as to modify the curvature of the leg opening, providing a separate strip of material defining a second bonding surface, bonding the second bonding surface on the separate strip of material to the first bonding surface on the web, and relaxing the web.

In yet another aspect, the present invention is directed to a method for bonding surfaces on a moving web including providing a web travelling in a machine direction which includes curved leg openings and which defines at least a first bonding surface adjacent each leg opening. For each leg opening, the method further includes deforming the web so as to modify the curvature of the leg opening, folding an edge portion of the web to form a strip adjacent the leg opening before, during or after deformation of the web, the strip defining a second bonding surface, bonding the second bonding surface on the folded strip to the first bonding surface on the web, and relaxing the web.

In still yet another aspect the present invention is directed to a method for making a disposable garment comprising providing an outer cover web, forming a pair of opposed curved leg openings in the web, the leg openings defining at least a first bonding surface adjacent each leg opening. For each leg opening the method also includes deforming the outer cover web so as to modify the shape of the leg opening, providing a strip defining a second bonding surface, bonding together at least portions of the first and second bonding surfaces of the modified leg opening, and relaxing the web.

Each strip may be a folded edge region of the web, in which case the method includes the step of folding the edge region of the web during, before or after the web is deformed. Alternatively, the strip may be separate from the web prior to bonding. In this case, the separate strip may comprise a strip of an elastic material, for example an elastic band or ribbon, elastic strands, or a composite elastic material, and the method may include the step of stretching the elastic material prior to bonding it to the moving web.

The moving web may be deformed so as to modify the shape of the leg openings by stretching in the machine direction or the cross-machine direction. The moving web may also be deformed by rotating, turning or twisting portions of the web. Typically, the web defines curved leg openings, and the step of deforming the web serves to reduce the degree of curvature of each leg opening.

In one aspect of the invention, the web is deformed to such an extent that each curved leg opening forms a straight or substantially straight edge.

The moving web may be deformed by a drum which includes projections, recesses, or inclined surfaces. Alternatively, the web may be deformed by means of diverging pins.

The strips may be bonded to the web by spaced-apart bonds, or they may be bonded to the web along at least one bonding line. Suitably, the strips and the web are bonded together by means of ultrasonic bonding, pressure bonding, thermal bonding, or by means of an adhesive.

In one aspect of the invention, the strips are curved on at least one puck prior to being bonded to the web. In this aspect of the invention, the strips may be cut from an elastic ribbon as they are applied to the puck.

Suitably, the web is a stretchable or gatherable outer cover for an absorbent garment such as a diaper, a training pant, an incontinence garment, swim wear or the like.

The broad scope of the applicability of the present invention will become apparent to those of skill in the art from the details given below.

The detailed description of the preferred embodiments of the invention is given by way of example only, and various modifications within the scope of the invention will be apparent to those of skill in the art.

BRIEF DESCRIPTION OF THE DRAWINGS

FIG. 5 is a diagrammatic side elevation view of a portion of an apparatus for attaching leg elastics to a web according to a second aspect of the invention.

FIG. 6 is a cross-sectional view along the line 6—6 in FIG. 5.

DEFINITIONS

Figure 1:
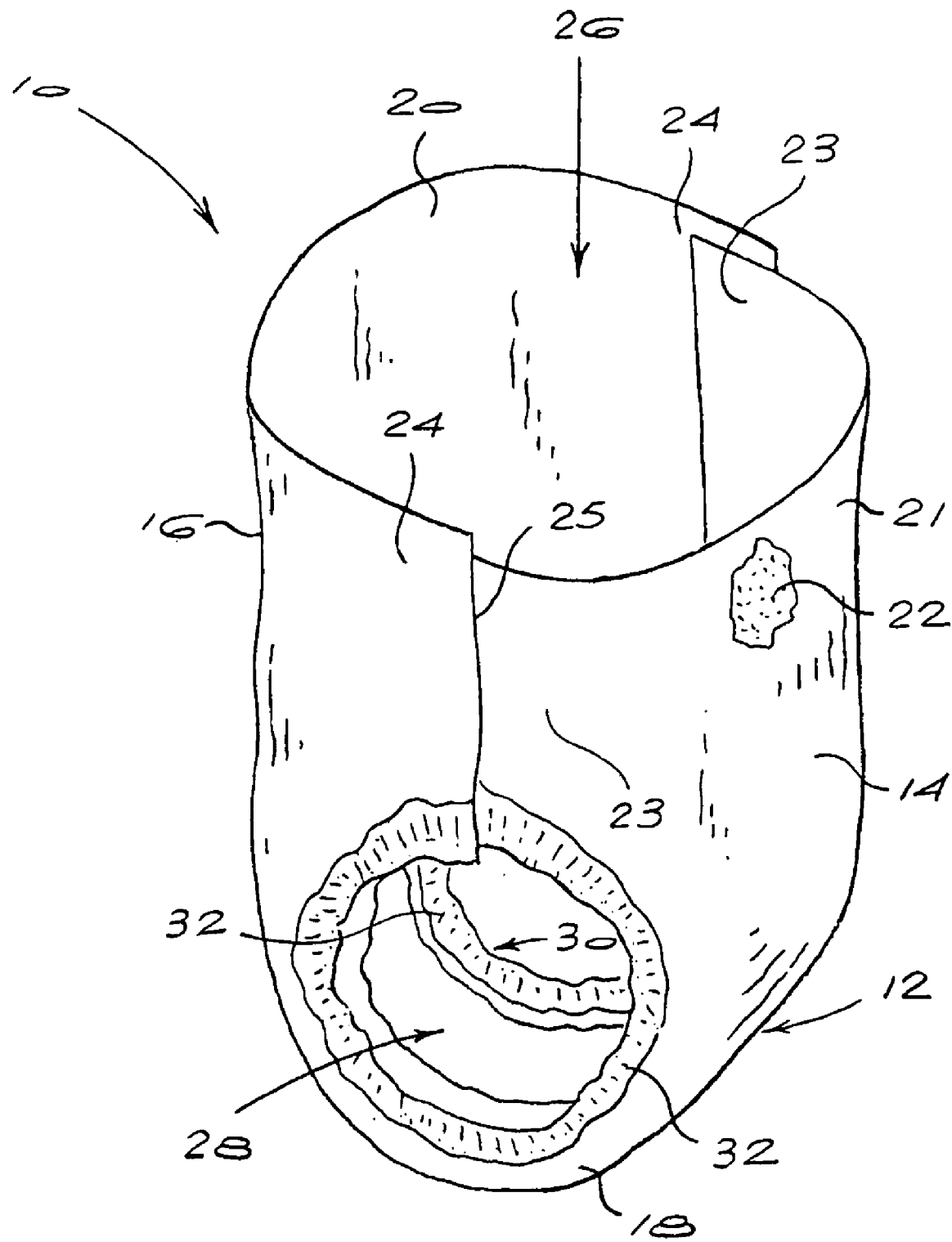
FIG. 1 is a perspective view of an absorbent garment.

As used herein, the term "bonding" means the joining, adhering, connecting, attaching or the like of surfaces on one or more elements.

As used herein, the term "disposable", when used to describe articles such as garments, means an article which is designed to be discarded after a limited use rather than being laundered or otherwise restored for use.

As used herein, the term "elastic", when used to describe a material, means that property of the material by virtue of which it tends to recover its original size and shape, or a high percentage thereof, after removal of a force causing deformation.

As used herein, the term "extensible", when used to describe a material, means a material that is capable of being extended or protruded in length or breadth.

As used herein, the term "flexible", when used to describe a material, means a material which is compliant and which will readily conform to the general shape and contour of a wearer's body.

As used herein, the term "liquid impermeable", when used to describe a layer or multi-layer laminate, means that a liquid, such as urine, will not pass through the layer or laminate, under ordinary use conditions, in a direction generally perpendicular to the plane of the layer or laminate at the point of liquid contact, and "liquid permeable" means a layer or laminate that is not liquid impermeable.

As used herein, the term "machine direction", when used with respect to a fabric or material, means the direction along the length of the fabric or material in which it is produced or converted, as opposed to "cross direction" or "cross-machine direction" which refers to the direction along the width of the fabric or material, generally perpendicular to the machine direction.

As used herein, the term "stretchable", when used to describe a material, means a material that can be stretched, without breaking, by at least 50% in at least one direction, suitably by at least 100%, and most suitably by at least 150%. The term "stretchable" includes elastic materials as well as extensible materials that stretch but do not significantly retract.

As used herein, the term "biaxial stretchability", when used to describe a material, means a material having stretchability in both the machine direction and the cross-machine direction.

As used herein, the term "comprising" is intended to be inclusive or open-ended, and is not intended to exclude additional elements or method steps which do not prevent operation of the invention.

DETAILED DESCRIPTION OF THE INVENTION

The present invention is directed to a method for forming leg portions on a garment, such as a disposable absorbent article. Examples of suitable articles for use with the present invention include, but are not limited to, diapers, training pants, feminine care products, incontinence products, disposable apparel, other personal care or health care garments, and the like. For ease of explanation, the description hereafter will be made with reference to a child's training pant. Generally, these garments include a pair of leg openings and an elastic portion around each leg opening for preventing leakage from the garment and for providing a finished look or appearance.

With reference to FIG. 1 of the drawings, a pant-like disposable absorbent article such as a training pant 10 is illustrated in a fastened condition. The absorbent article includes a chassis 12 which defines a front region 14, a rear region 16, and a crotch region 18 interconnecting the front and rear regions. The chassis 12 includes a liquid permeable bodyside liner 20 for contacting a wearer's body, and a liquid impermeable outer cover 21 for contacting the wearer's clothing. An absorbent assembly 22 may be sandwiched between the bodyside liner 20 and the outer cover 21. The absorbent article 10 includes transversely opposed, front side panel portions 23 on the front region 14 of the chassis 12, and transversely opposed rear side panel portions 24 on the rear region 16 of the chassis 12. The front and rear side panel portions 23 and 24 are releasably attachable to one another by a fastening system 25. The absorbent chassis 12 and the fastening system 25 together define a refastenable pant having a waist opening 26, and a pair of leg openings 28 and 30. Alternatively, the front side panel portions 23 may be permanently bonded to the rear side panel portions 24 to form a closed pant-like disposable absorbent article. Leg elastics 32 extend around the leg openings 28 and 30 of the absorbent article 10 to create gaskets for reducing or preventing leakage around the leg openings, between the absorbent article 10 and the legs of the wearer. Generally, curved leg elastics are more form-fitting than straight leg elastics, and the leg openings are gathered with less tension, resulting in an absorbent garment with increased comfort.

The outer cover 21 of the absorbent article 10 suitably comprises a material which is substantially liquid impermeable. The outer cover 21 can be a single layer of liquid impermeable material, but more suitably comprises a multi-layered laminate structure in which at least one of the layers can be liquid impermeable. For instance, the outer cover 21 can include a liquid permeable outer layer and a liquid impermeable inner layer that are suitably joined together by a laminate adhesive, ultrasonic bonds, thermal bonds, or the like. The liquid permeable outer layer can be any suitable material and desirably is one that provides a generally cloth-like texture, for example a 20 grams per square meter (gsm) spunbond polypropylene nonwoven web. The inner layer of the outer cover 21 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 21 when a single layer, prevents waste material from wetting articles, such as bed sheets and clothing, as well as the wearer and caregiver. One example of a liquid impermeable film for use as a liquid impermeable inner layer, or a single layer liquid impermeable outer cover 21, is a 0.02 millimeter polyethylene film commercially available from Pliant Corporation of Schaumburg, Ill., U.S.A.

More suitably, the outer cover 21 is stretchable or gatherable, and even more suitably the outer cover is elastic. For example, the outer cover 21 may be constructed of a single layer, multiple layers, laminates, films, nonwoven fabrics, elastic netting, microporous webs, bonded carded webs or foams comprised of elastomeric or polymeric materials. The materials may be extensible or stretchable in one direction or they may be biaxially extensible or stretchable. Elastomeric non-woven laminate webs can include a non-woven material joined to one or more gatherable non-woven webs, films, or foams. Stretch Bonded Laminates (SBL) and Neck Bonded Laminates (NBL) are examples of elastomeric composites. A non-woven fabric is any web of material which has been formed without the use of a textile weaving process which produces a structure of individual fibers that are interwoven in an identifiable repeating manner.

Examples of suitable materials are spunbond-meltblown fabrics, spunbond-meltblown-spunbond fabrics, spunbond fabrics, or laminates of such fabrics with scrims, films, foams, or other non-woven webs. Elastomeric materials may include cast or blown films, foams, or meltblown fabrics composed of polyethylene, polypropylene, or polyolefin copolymers, as well as combinations thereof. The elastomeric materials may include PEBAX® elastomer (available from AtoChem located in Philadelphia, Pa.), HYTREL® elastomeric polyester (available from E. I. DuPont de Nemours of Wilmington, Del.), KRATON® elastomer (available from Kraton Polymers of Houston, Tex.), or strands of LYCRA® elastomer (available from E. I. DuPont de Nemours of Wilmington, Del.), or the like, as well as combinations thereof. The outer cover 21 may include materials that have elastomeric properties through a mechanical process, printing process, heating process, or chemical treatment. For example, such materials may be apertured, creped, neck-stretched, heat activated, embossed, and micro-strained; and may be in the form of films, webs, and laminates.

In one aspect of the invention, the outer cover 21 may comprise a 13.6 gsm basis weight layer of G2760 KRATON elastomer strands adhesively laminated with a 0.3 gsm layer of adhesive to at least one facing. The facing can be composed of a thermal point bonded bicomponent spunbond non-woven fibrous web having a 23.7 gsm basis weight.

The bodyside liner 20 of the absorbent article 10 is suitably compliant, soft-feeling, and non-irritating to the wearer's skin. The bodyside liner 20 is also sufficiently liquid permeable to permit liquid body exudates to readily penetrate through its thickness to the absorbent assembly 22. A suitable bodyside liner 20 may be manufactured from a wide selection of web materials, such as porous foams, reticulated foams, apertured plastic films, woven and non-woven webs, or a combination of any such materials. For example, the bodyside liner 20 may comprise a meltblown web, a spunbonded web, or a bonded-carded-web composed of natural fibers, synthetic fibers or combinations thereof. The bodyside liner 20 may be composed of a substantially hydrophobic material, and the hydrophobic material may optionally be treated with a surfactant or otherwise processed to impart a desired level of wettability and hydrophilicity.

The bodyside liner 20 may also be stretchable, and more suitably it may be elastic. Elastomeric materials suitable for constructing the bodyside liner 20 include elastic strands, LYCRA elastics, cast or blown elastic films, nonwoven elastic webs, meltblown or spunbond elastomeric fibrous webs, as well as combinations thereof. Examples of suitable elastomers include KRATON elastomers, HYTREL elastomers, ESTANE® elastomeric polyurethanes (available from B.F. Goodrich and Company of Cleveland, Ohio), or PEBAX elastomers.

The bodyside liner 20 and the outer cover 21 may be attached to one another along at least a portion of their periphery by adhesive, ultrasonic bonding, thermal bonding or other suitable attachment means known in the art.

The absorbent assembly 22 is suitably compressible, conformable and capable of absorbing and retaining liquid body exudates released by the wearer. The absorbent assembly may comprise a single, integral piece of material, or alternatively it may comprise a plurality of individual separate pieces of material which are operatively assembled together.

In one aspect of the invention, the absorbent assembly 22 comprises a matrix of hydrophilic fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A., and is a bleached, highly absorbent sulfate wood pulp containing primarily soft wood fibers and about 16 percent hardwood fibers. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The superabsorbent material may be present in the absorbent assembly 22 in an amount of from 0 to about 100 weight percent based on total weight of the absorbent assembly. The absorbent assembly 22 suitably has a density within the range of about 0.10 to about 0.5 grams per cubic centimeter and may or may not be wrapped or encompassed by a suitable tissue or nonwoven wrap for maintaining the integrity and/or shape of the absorbent structure.

A wide variety of elastic materials may be used for the leg elastics 32. Suitable elastic materials include sheets, strands or ribbons of natural rubber, synthetic rubber, or thermoplastic elastomeric polymers. In one aspect of the invention, the leg elastics may include a plurality of dry-spun coalesced multi-filament spandex elastomeric threads sold under the trade name LYCRA and available from E.I. DuPont de Nemours and Company, Wilmington, Del., U.S.A.

The fastening system 25 may comprise any refastenable fasteners suitable for absorbent articles, such as adhesive fasteners, cohesive fasteners, mechanical fasteners, or the like. In one aspect of the invention, the fastening system comprises mechanical fastening elements for improved performance. Suitable mechanical fastening elements can be provided by interlocking geometric-shaped materials, such as hooks, loops, bulbs, mushrooms, arrowheads, balls on stems, male and female mating components, buckles, snaps, or the like. Children's training pants are also described in U.S. Pat. No. 4,940,464 to Van Gompel, et al., and Pat. No. 6,645,190 to Olson, et al., the disclosures of which are incorporated by reference to the extent they are consistent (i.e., not in conflict) herewith.

Figure 2:
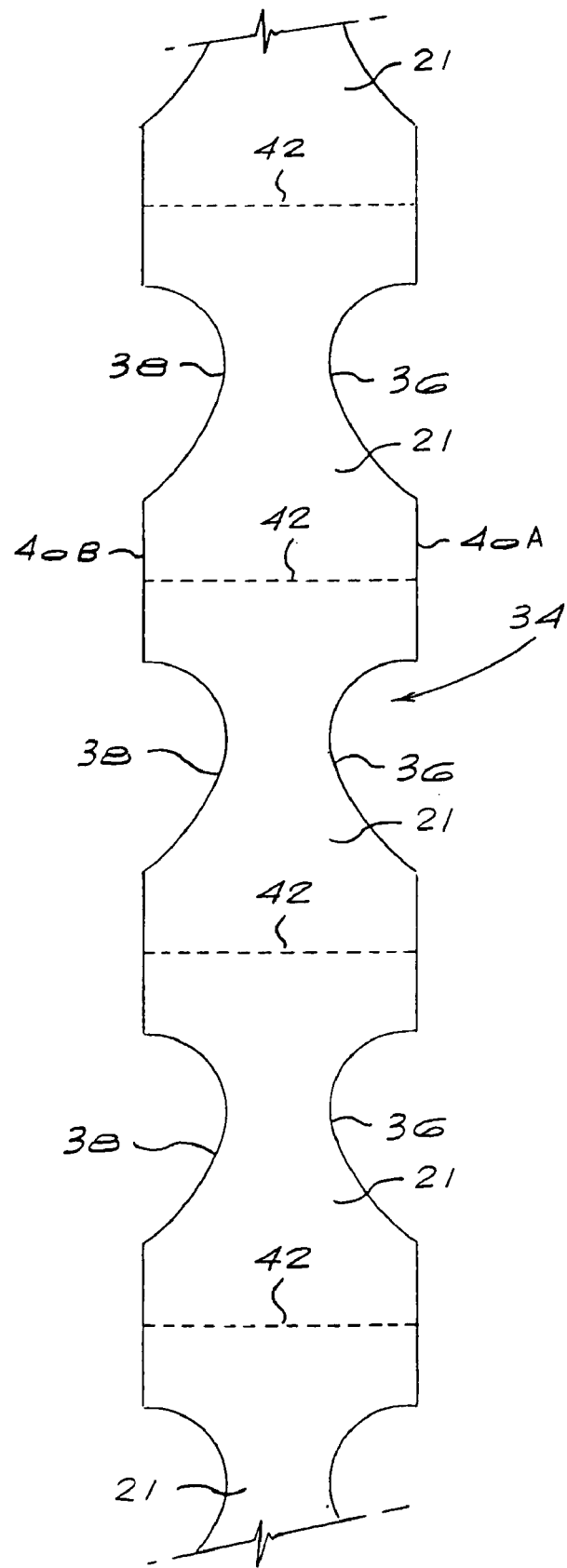
FIG. 2 is a top view of a web for forming outer covers for absorbent garments of the type illustrated in FIG. 1, showing the web with curved leg openings in a relaxed condition.

FIG. 2 illustrates a web 34 for forming outer covers 21 for absorbent articles of the type illustrated in FIG. 1. As can be seen, the web 34 includes a plurality of curved leg openings 36 and 38 provided therein along the substantially parallel side edges 40A and 40B. The web may be provided with leg openings 36 and 38 pre-formed, or the leg openings may be otherwise provided as is know in the art. For example, the leg openings may be formed using water cutters, die cutters, ultrasonic cutting, and the like, or combinations thereof. In this aspect of the invention, the web 34 is designed to be cut transversely along its length, as indicated by the broken lines 42, to form waist edges on the outer covers 21.

Figure 3:
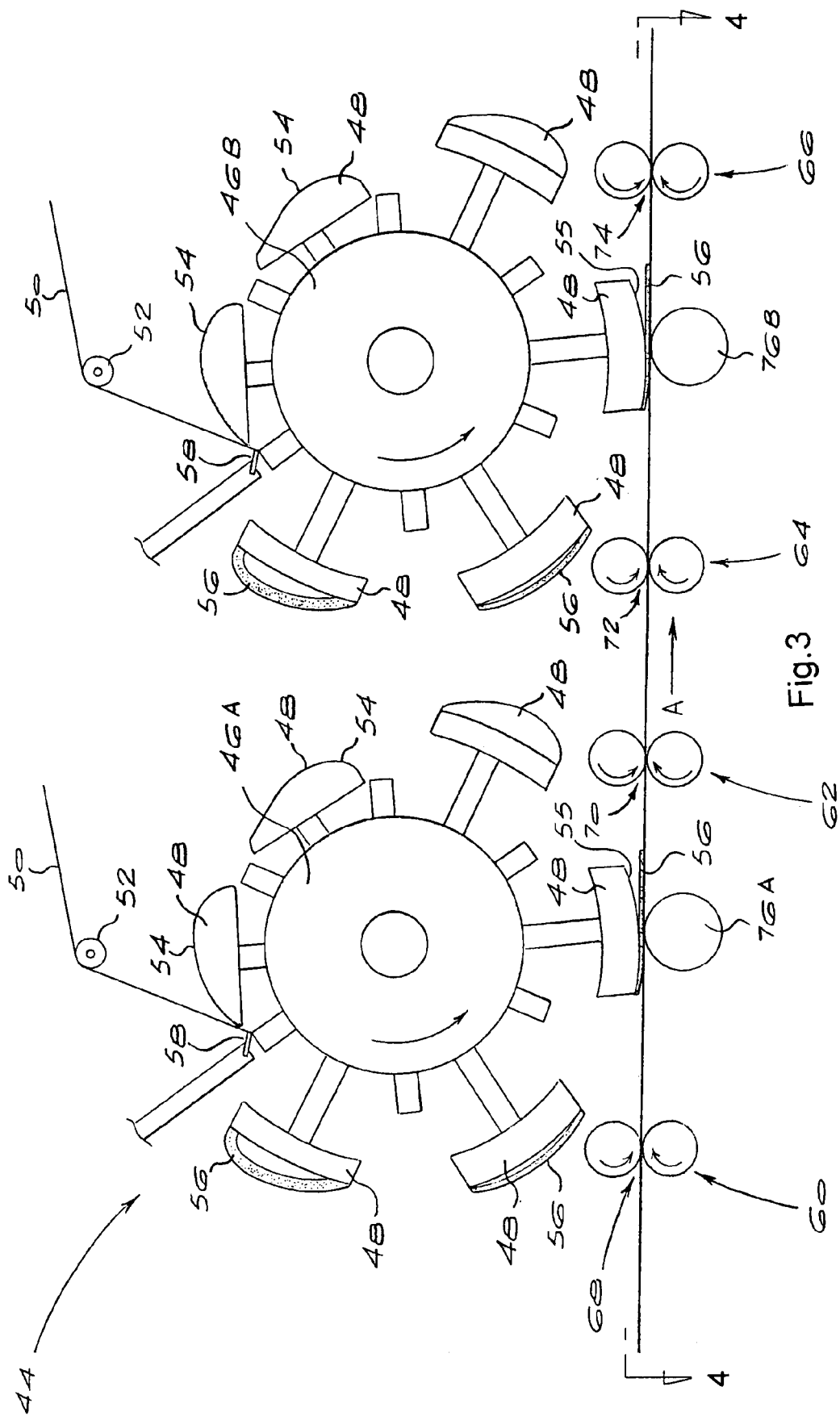
FIG. 3 is a diagrammatic side elevation view of a portion of an apparatus for attaching leg elastics to a web according to a first aspect of the invention.
Figure 4:
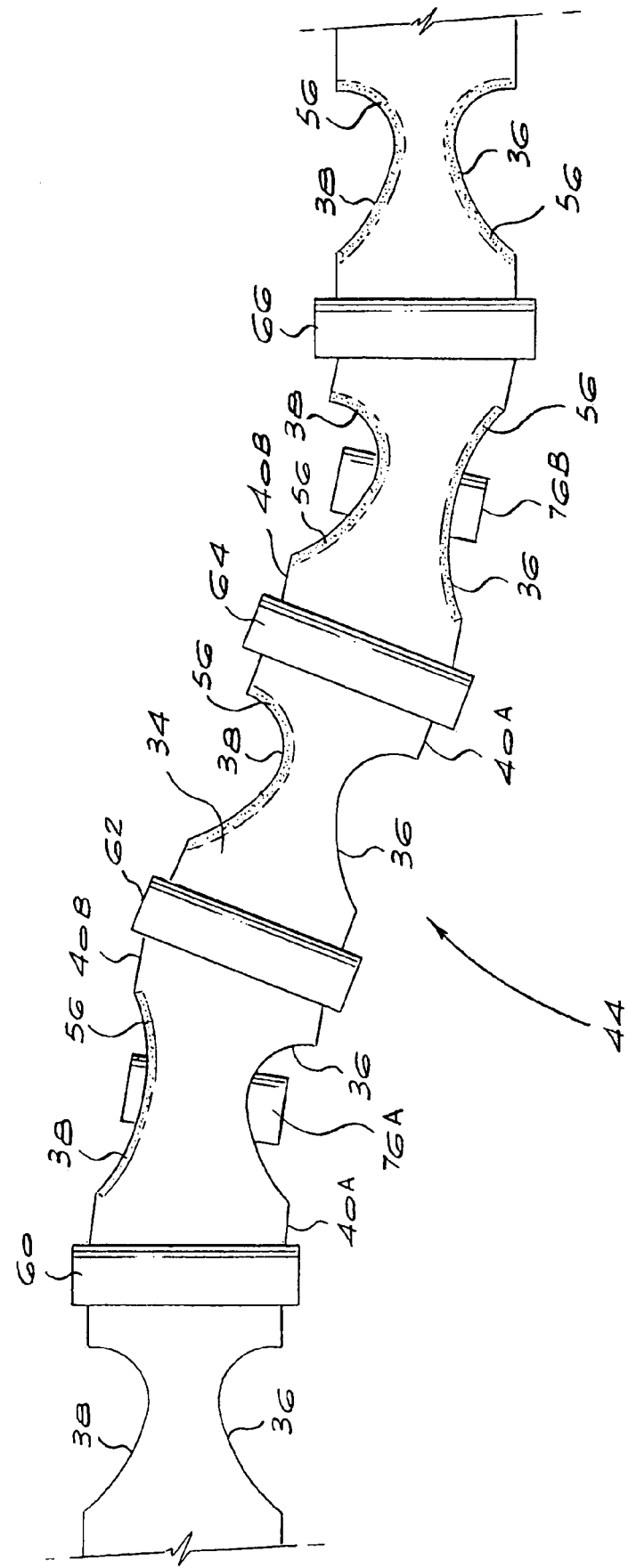
FIG. 4 is a cross-sectional view along the line 4—4 in FIG. 3.

A portion of one example of an apparatus for carrying out the method of the present invention is illustrated in FIGS. 3 and 4. The apparatus is designated generally with the reference numeral 44 and includes a pair of rotating devices 46A and 46B carrying semi-curved pucks 48. "Semi-curved" refers to a puck having at least one curved surface which extends partially around the puck, but less than all the way around the puck. The semi-curved pucks 48 desirably have curved contours on at least two adjacent surfaces. The curved surfaces may vary in degrees of curvature along their lengths, with optimal curvature of a first of the curved surfaces 54 of each puck 48 conforming to the curvature of one of the leg openings 36 and 38 on the web 34, and optimal curvature of a second of the curved surfaces 55 of each puck 48 being such that it forms a rolling action when the puck is in position to transfer and bond a strip of elastic ribbon to the web 34. Each rotating device 46A and 46B rotates in a direction complementary to the machine direction travel of the web 34, as indicated generally by the arrow "A" in FIG. 3.

The rotating devices 46A and 46B carrying the pucks 48 may be similar to those described in U.S. Pat. No. 6,533,879 to Quereshi et al, the contents of which are incorporated herein by reference to the extent that they are consistent with the present disclosure. For each rotating device 46A and 46B, an elastic ribbon 50 can be fed to the pucks 48 via a guide roll 52, and the elastic ribbon can be deflected onto each rotating puck, so as to follow the contours of the first curved surface 54 of the puck, and can be cut into a strip 56 by a cutting device 58. Examples of suitable cutting devices include mechanical pinch-type cut-off knives, shear-type cut-off knives, and hot knives or other cutting means well known in the art. The elastic strips 56 suitably are stretched to at least 125%, more suitably at least 150%, of their initial (unstretched) length as they are applied to the pucks 48.

A vacuum within the pucks 48 can be used to hold the elastic strips 56 in place on the pucks. Alternatively, or additionally, each puck may have a non-slip texture on at least part of the second curved surface thereof for holding the elastic strips 56 in place.

Each elastic strip 56 can then be carried on a puck 48 by the rotating device 46A or 46B into engagement with the moving web 34, and can be deposited onto the moving web along a curvilinear path so as to form a curved leg elastic on the web. As each puck 48 is displaced from the elastic-application position to the web-bonding position, the puck is radially displaced to increase the pitch. At the same time, the puck 48 is rotated approximately 45–135 degrees from a position in which the first curved surface 54 of the puck is at a radially outermost position, to a position in which the second curved surface 55 of the puck is at a radially outermost position for bonding the elastic strip 56 to the moving web in a manner which is described in more detail below.

As the elastic strips 56 are bonded to the moving web 34, the rotating device 46A or 46B continues to rotate the pucks 48, advancing the pucks from the web-bonding position back towards the elastic-application position, and the pucks 48 are returned to their initial alignment in which the first curved surface 54 of each puck 48 is at a radially outermost position. In this way, as each puck 48 returns to the elastic-application position, it receives the next elastic strip 56, and so the process continues.

Each of the pucks 48 can be actuated to oscillate individually using stationary spiral cam tracks and multiple cam followers positioned around a pivot point of an arm supporting each of the pucks. The rotating devices 46A and 46B can each be a high efficiency interface roll, as disclosed in U.S. Pat. No. 5,556,504 to Rajala et al. Other examples of suitable rotating devices are disclosed in U.S. Pat. No. 5,716,478 to Boothe et al and U.S. Pat. No. 5,759,340 to Boothe et al. Additionally, cam boxes, gear racks, bevel gears, and hinge points with plows are other examples of suitable rotating devices.

Bonding devices 76A and 76B, such as ultrasonic bonders, are located in close proximity to the rotating devices 46A and 46B, and typically are positioned below the web 34, as shown in FIGS. 3 and 4. The pucks 48 can either rotate onto the moving web 34 with sufficient pressure for the bonding process, or each bonding device can exert an upward force to carry out the bonding process.

The apparatus 44 also includes four sets of rollers 60, 62, 64 and 66 which are configured to alter the machine direction of the web 34 in a manner which is described in more detail below. The first set of rollers 60 form a nip 68 which defines a slightly smaller gap than the thickness of the web 34. The second, third and fourth sets of rollers 62, 64 and 66 also define nips 70, 72 and 74 which are similar to the nip 68. With particular reference to FIG. 4 of the drawings, the second set of rollers 62 can be inclined relative to the first set of rollers 60, and the fourth set of rollers 66 can be inclined relative to the third set of rollers 64. Each set of rollers 60, 62, 64 and 66 includes an upper roller which is rotated in a first direction, and a lower roller which is rotated in an opposite, second direction so that both the upper and the lower rollers engage the web 34 in the machine direction. The rollers may be formed from any suitable material, such as, for example, a plastic material, a metallic material, combinations of these materials, or the like.

Each set of rollers may receive drive from a drive arrangement (not illustrated) which may include a motor, for example an electric motor, for driving an axle of each roller via a drive shaft, and a set of gears.

In practice, the moving web 34 can be deformed by stretching the side edges 40A and 40B thereof so as to reduce the curvature of the leg openings 36 and 38 prior to depositing and bonding the leg elastics 56 to the web. With particular reference to FIG. 4, as the web 34 emerges from the set of rollers 60, it can be pulled to one side by the set of rollers 62 so that the side edge 40B is stretched, deforming the web so as to elongate the leg openings 38 between the set of rollers 60 and 62. The elongation of each leg opening 38 reduces the degree of curvature of the leg opening, as shown.

The rotating device 46A and the bonding device 76A can be arranged so that, as a leg opening 38 is elongated on the stretched web 34, one of the pucks 48 engages the web, immediately above the bonding device, to deposit an elastic strip 56 onto the web, adjacent the elongate leg opening, and to bond the elastic strip to the web, as shown in FIG. 4. The bonds formed as the puck 48 deposits the elastic strip 56 onto the web 34 are strong enough to separate the elastic strip from the vacuum in the puck 48, or alternatively from the non-slip texture of the puck. As a further alternative, the vacuum in the puck 48 can be released as the elastic strip 56 is deposited onto the web 34.

When the web 34 emerges from the set of rollers 62, the tension in the web is relaxed and the leg opening 38 contracts from its stretched, elongate condition. The web 34 can then pass through the set of rollers 64 and can be pulled to the other side by the set of rollers 66 so that the side edge 40A is stretched, deforming the web and elongating the leg openings 36. Similarly to the leg openings 38, the elongation of each leg opening 36 reduces the degree of curvature of the leg opening.

The rotating device 46B and the bonding device 76B operate to bond elastic strips 56 to the web 34, adjacent the elongate leg openings 36, in a similar manner to that described above with reference to the leg openings 38. Accordingly, as a leg opening 36 is elongated on the stretched web 34, one of the pucks 48 engages the web, immediately above the bonding device 76B, to deposit a leg elastic strip 56 onto the web, adjacent the elongate leg opening 36, and to bond the elastic strip to the web. In this way, elastic strips 56 can be bonded to both side edges 40A and 40B of the moving web 34 as it passes through the apparatus 44. When the web 34 emerges from the set of rollers 66, the tension in the moving web can be relaxed and the leg openings 36 contract from their stretched, elongate condition.

The stretching of the moving web 34 as it passes through the apparatus 44 facilitates high speed bonding of the elastic strips 56 to the web by reducing the degree of curvature of the leg openings 36 and 38 prior to bonding. This allows for reduced curvatures on the curved surfaces of the pucks 48, simplifying apparatus for applying the elastic strips 56. Furthermore, reducing the degree of curvature of the leg openings 36 and 38 prior to bonding can prevent sharp direction changes in the application of the elastic strips 56, thereby reducing shear loading and associated mechanical stresses in the web.

The method of the invention is not limited to the use of rotating devices and pucks of the type described above and in U.S. Pat. No. 6,533,879. It should be appreciated that once the moving web 34 is deformed and the leg openings 36 and 38 are elongated, any suitable apparatus for applying a curved leg elastic to the web may be used. Examples of other devices that could be used include the devices disclosed in U.S. Pat. No. 4,578,133 to Oshefsky et al and U.S. Pat. No. 6,540,857 to Coenen et al. It will also be appreciated that the leg elastics 56 need not be bonded to the web 34 by ultrasonic bonding, and that other types of bonding could be used, such as adhesive bonding, thermal bonding, pressure bonding or other conventional techniques. Suitable adhesives include spray adhesives, hot melt adhesives, self-adhering elastomeric materials and the like. It will also be understood that, with suitable modifications, the rollers 64 could be omitted so that the web 34 passes directly from a condition in which the side edge 40B is stretched on one side of the rollers 62 to a condition in which the side edge 40A is stretched on the other side of the rollers 62.

FIGS. 5 and 6 illustrate components of an apparatus for carrying out a method in accordance with a second aspect of the invention. The apparatus is designated generally with the reference numeral 144 and is similar in many respects to the apparatus 44 described above with reference to the first aspect of the invention. However, the apparatus 144 includes four sets of rollers 160, 162, 164 and 166 which are inclined relative to one another, and which are spaced from one another, so as to deform a moving web 134 to such an extent that curved leg openings 136 and 138 on the web are pulled straight or substantially straight, as shown in FIG. 6. Apart from their relative inclination and spacing, the sets of rollers 160, 162, 164 and 166 are similar in all other respects to the sets of rollers 60, 62, 64 and 66 of the first aspect of the invention. Accordingly, each set of rollers 160, 162, 164 and 166 forms a nip defining a slightly smaller gap than the thickness of the web 134, and each set of rollers 160, 162, 164 and 166 includes an upper roller which is rotated in a first direction, and a lower roller which is rotated in an opposite, second direction so that both the upper and the lower rollers engage the web 134 in the machine direction, as indicated generally by the arrow "B" in FIG. 5. The sets of rollers 160, 162, 164 and 166 may also receive drive from a drive arrangement (not illustrated) which may include a motor, for example an electric motor, for driving an axle of each roller via a drive shaft, and a set of gears.

In this aspect of the invention, a rotatable drum 180A is arranged to engage the web 134 between the sets of rollers 160 and 162, immediately above a bonding device 176A, and a rotatable drum 180B is arranged to engage the web 134 between the sets of rollers 164 and 166, immediately above a bonding device 176B. The drums 180A and 180B rotate in a direction complementary to the machine direction movement of the web 134, and may be driven by any suitable drive means (not illustrated). The drive means for each drum 180A and 180B may include an electric motor (not shown) which transmits drive to the drum via a gearbox (also not shown).

Elastic ribbons 150 can pass over guide rolls 152 as they are fed towards the drums 180A and 180B, and the ribbons 150 can be deflected onto the drums and can be cut into elastic strips 156 by cutting devices 158. The cutting devices 158 may be mechanical pinch-type cut-off knives, shear-type cut-off knives, hot knives or other cutting means well known in the art. The elastic ribbons 150 suitably are stretched to at least 125%, more suitably at least 150%, of their initial (unstretched) length as they are applied to the drums 180A and 180B, and the elastic ribbons 150 are received on the drums 180A and 180B as straight or substantially straight elastic strips 156 which are rotated on the drums into contact with the moving web 134 for bonding to the web. The outer surface of each drum 180A and 180B may have a non-slip texture on at least a part of this surface for holding the elastic strips 156 in place. Alternatively, vacuum pressure may be used to hold the elastic strips 156 in place.

The drums 180A and 180B and the bonding devices 176A and 176B are arranged so that the elastic strips 156 are brought into contact with the web 134, and are bonded to the web 134, adjacent the stretched leg openings 136 and 138, as shown in FIG. 6, with bonds that are strong enough to separate the elastic strips 156 from the non-slip textured surfaces of the drums 180A and 180B.

Similarly to the web 34 in the first aspect of the invention described above, the web 134, as it passes through the sets of rollers 160, 162, 164 and 166, can be pulled first in one direction so as to stretch the leg openings 138 for application of the elastic strips 156 to the web adjacent these leg openings, and can then be pulled in the opposite direction so as to stretch the leg openings 136 for application of the elastic strips 156 to the web adjacent these leg openings. This process is illustrated most clearly in FIG. 6, which also shows how the initial curvatures of the leg openings are restored when the web 134 exits the set of rollers 166 and is relaxed.

It will be understood by those of skill in the art that the web could also be stretched along its centerline. For example, the rollers illustrated in FIGS. 3 and 4 could be spaced from one another, without any relative inclination, so as to stretch the web 34 in the machine direction, elongating both sets of leg openings 36 and 38 simultaneously. Similarly, the rollers illustrated in FIGS. 5 and 6 could be spaced from one another, without any relative inclination, so as to stretch the web 134 in the machine direction, elongating both sets of leg openings 136 and 138 simultaneously.

Figure 8:
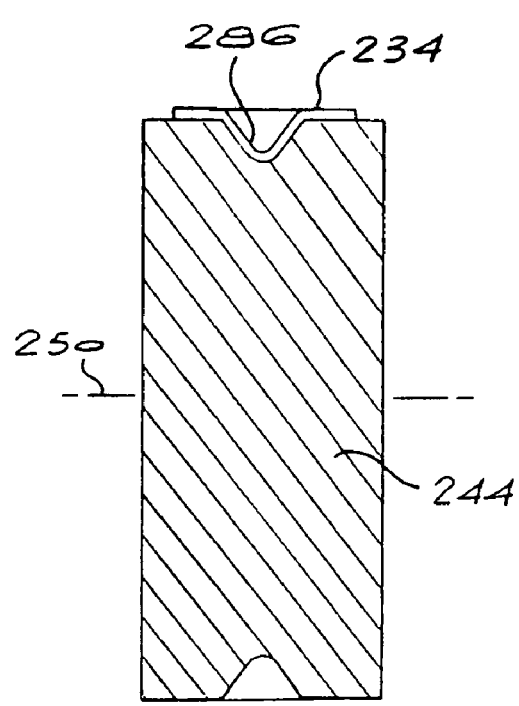
FIG. 8 is a cross-sectional view along the line 8—8 in FIG. 7.
Figure 7:
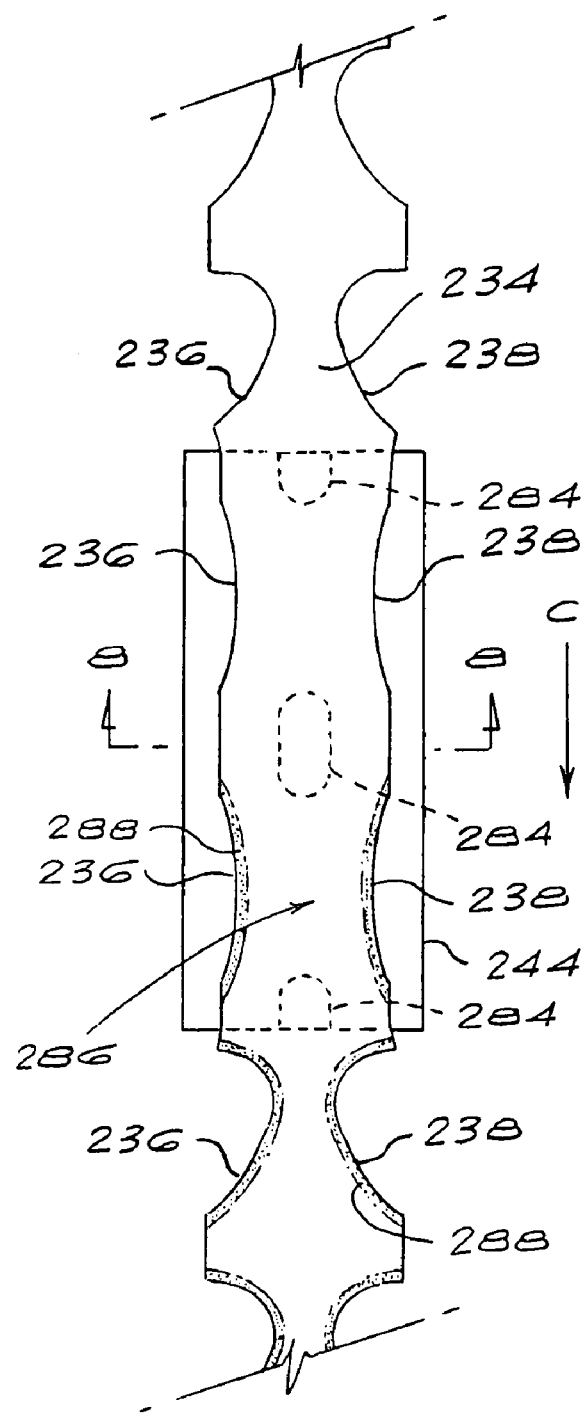
FIG. 7 is a top view of a component forming part of an apparatus for attaching leg elastics to a web according to a third aspect of the invention.

FIGS. 7 and 8 illustrate a wheel 244 for deforming a moving web 234 in a method according to a third aspect of the invention. As representatively illustrated in FIGS. 7 and 8, the wheel 244 defines a plurality of recesses 284 which are aligned with the machine direction of the web 234, as indicated by the arrow "C" in FIG. 7. The wheel 244 may be formed from any suitable material such as, for example, a plastic material, and it may be rotated by a drive motor (not shown), or it may be free to rotate about an axis 250. A vacuum within the wheel 244 can be used to hold the moving web 234 on the wheel so that portions of a central region 286 of the web are positioned within the recesses 284, as illustrated in FIG. 8. Alternatively, portions of the central region 286 of the web 234 may be pressed into the recesses 284, or the web 234 may be composed so that portions of the central region 286 thereof fall into these recesses of their own accord.

In practice, as the moving web 234 passes over the wheel 244, portions of the central region 286 of the web can be sucked into the recesses 284 to deform the web and modify the shape of curved leg openings 236 and 238 on the web. Leg elastics 288 are bonded to the moving web 234, adjacent the elongate leg openings 236 and 238, as the web travels over the wheel 244. Suitably, the leg elastics are applied to the web 234 with pucks (not illustrated) similar to those described above with reference to the first aspect of the invention.

As the web 234 moves off the wheel 244, it can be relaxed so that the leg openings 236 and 238 contract from their elongate condition, as illustrated in FIG. 7.

Instead of the recesses 284, the wheel 244 could include a plurality of projections for deforming portions of the central region 286 of the web 234.

Figure 9:
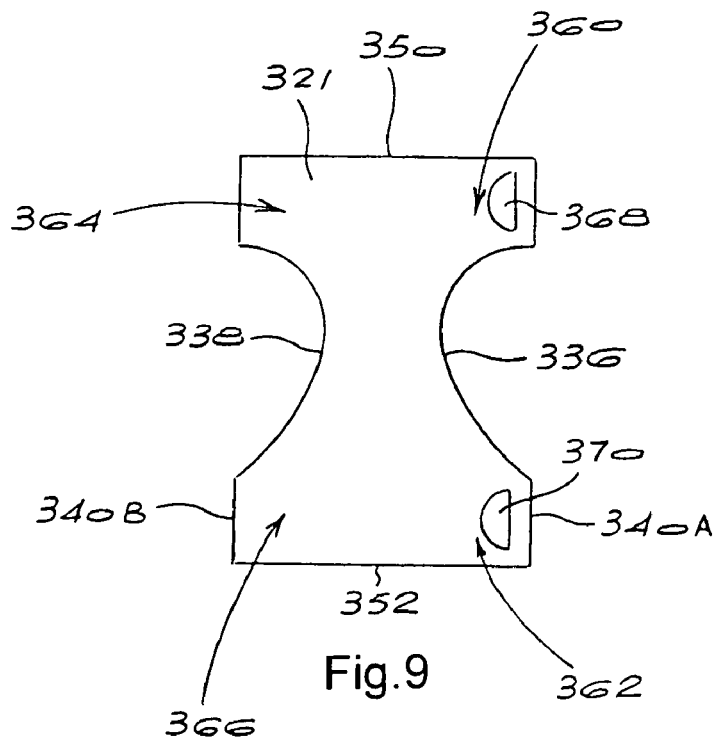
FIG. 9 is a top view of an outer cover for an absorbent garment of the type illustrated in FIG. 1, showing the outer cover in a relaxed condition.

FIG. 9 illustrates a stretchable outer cover 321 for an absorbent article of the type illustrated in FIG. 1 which can be stretched as a single piece in accordance with further aspects of the present invention. The outer cover 321 has a generally hourglass shape and includes curved leg openings 336 and 338 in substantially parallel side edges 340A and 340B thereof. As representatively illustrated in FIG. 9, the outer cover 321 defines a front edge 350 and a rear edge 352 for forming a front waist edge and a rear waist edge, respectively, in the absorbent article formed from the outer cover.

As in the first and second aspects of the invention, elastic strips (not illustrated) can be applied to the outer cover 321 after the outer cover has been stretched to elongate the curved leg openings 336 and 338. Suitably, the leg elastics are applied to the outer cover with pucks (not shown) in a manner similar to that described above with reference to the first embodiment of the invention. Prior to applying the leg elastics, the outer cover 321 can be deformed by displacing a front side portion 360 of the outer cover relative to a rear side portion 362 thereof, and displacing a front side portion 364 of the outer cover relative to a rear side portion 366 thereof. Suitably, the front side portion 360 and the rear side portion 362 are displaced relative to one another for application of a leg elastic to the outer cover 321 adjacent the leg opening 336, and subsequently the front side portion 364 and the rear side portion 366 are displaced relative to one another for application of an elastic strip to the outer cover 321 adjacent the leg opening 338.

Figure 10:
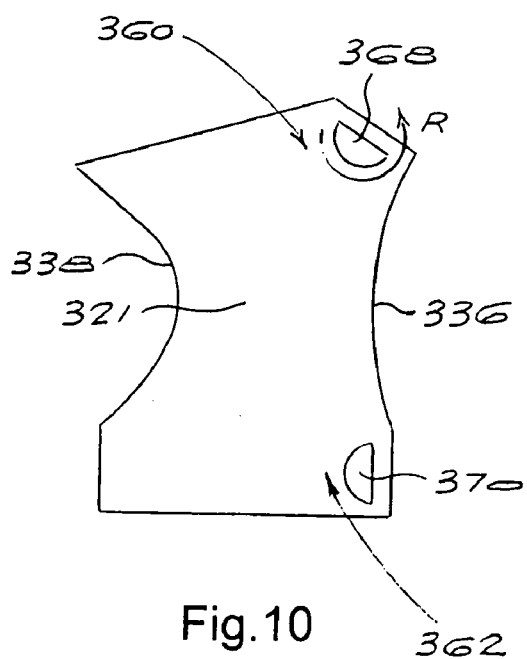
FIGS. 10 and 11 show the outer cover of FIG. 9 in two different stretched conditions.

The front side portions may be displaced relative to the rear side portions in various different ways. For example, FIG. 10 illustrates how the front side portion 360 of the outer cover 321 can be rotated in the direction of the arrow "R" by a puck 368 which, together with a puck 370, can be rotated into engagement with the web 321 in the configuration illustrated in FIG. 9, and subsequently can be rotated so as to twist the front side portion 360 of the web into the FIG. 10 configuration. The rear side portion 362 may be restrained by the puck 370, as representatively illustrated in FIG. 10, or it may be rotated by the puck 370 in an opposite sense to that of the front side portion 360. Once an elastic strip has been applied to the outer cover 321, adjacent the leg opening 336, and the stretched leg opening 336 is relaxed, the front side portion 364 may be displaced relative to the rear side portion 366 in a similar manner for application of a leg elastic to the outer cover, adjacent the leg opening 338.

Figure 11:
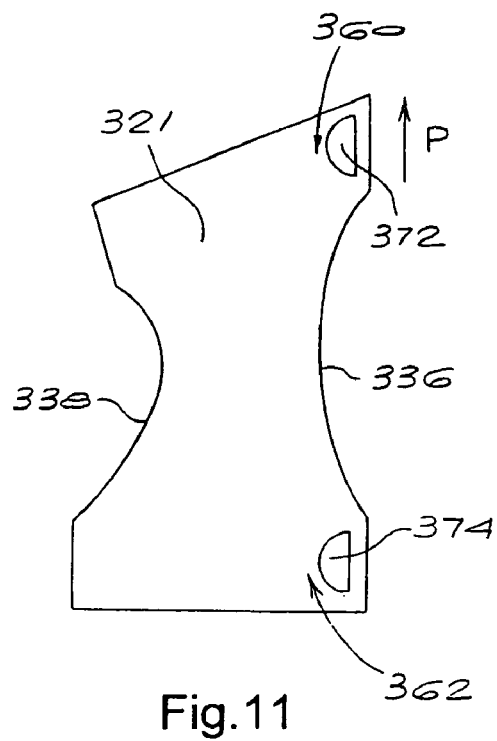

FIG. 11 illustrates how the front side portion 360 of the outer cover 321 can be drawn away from the rear side portion 362 by a pivoting puck 372 which, together with a puck 374, can be rotated into engagement with the web 321, and subsequently can be pivoted away from the puck 374 in the direction of the arrow "P" so as to displace the front side portion 360 relative to the rear side portion 362, as shown. Once an elastic strip has been applied to the outer cover 321, adjacent the leg opening 336, and the stretched leg opening 336 is relaxed, the front side portion 364 may be displaced relative to the rear side portion 366 in a similar manner for application of a leg elastic to the outer cover, adjacent the leg opening 338.

The aspects of the invention described above relate to methods in which webs of outer covers for absorbent articles, or individual outer covers for absorbent articles, are stretched in a machine direction. Methods in which webs of outer covers for absorbent articles are stretched in a cross-machine direction will now be described with reference to FIGS. 12 to 15 of the accompanying drawings.

Figure 12:
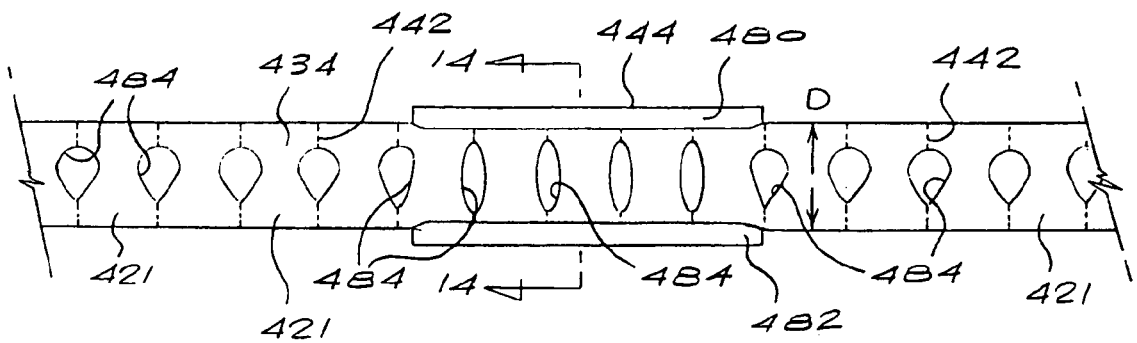
FIG. 12 is a top view of a component forming part of an apparatus for attaching leg elastics to a web according to a further aspect of the invention.
Figure 13:
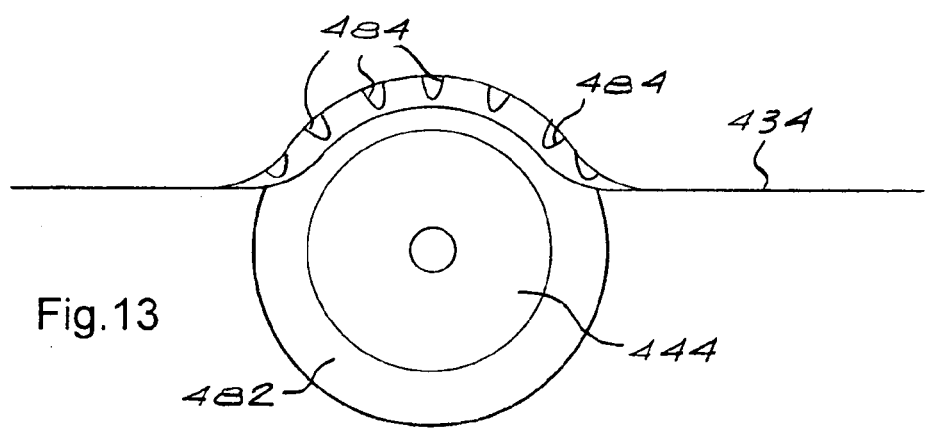
FIG. 13 is a side elevation view of the component illustrated in FIG. 12.
Figure 14:
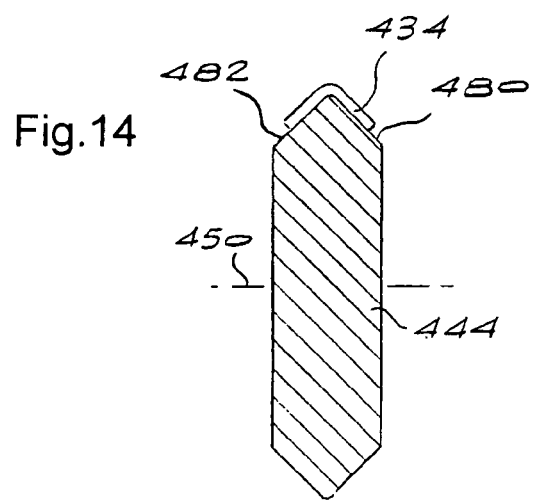
FIG. 14 is a cross-sectional view along the line 14—14 in FIG. 12.

FIGS. 12 to 14 illustrate a moving web 434 which is stretched in a cross-machine direction, as illustrated by the arrow "D" in FIG. 12, by a rotating wheel 444. The web 434 is designed to be cut transversely along its length at the broken lines 442 to form separate outer covers 421, and a plurality of apertures 484 in the web 434 define leg openings for adjacent outer covers 421. The wheel 444 includes two opposed, inclined surfaces 480 and 482 on the outer periphery thereof, and may be rotated by a drive motor (not shown), or it may be free to rotate about an axis 450.

As the moving web 434 passes over the wheel 444, it is deformed by the inclined surfaces 480 and 482 so as to be stretched in the cross-machine direction, as shown most clearly in FIG. 12. When the web 434 stretches in the cross-machine direction, the curved leg openings defined by the apertures 484 elongate to facilitate the application of leg elastics (not illustrated) to the web 434, adjacent the apertures 484.

Figure 15:
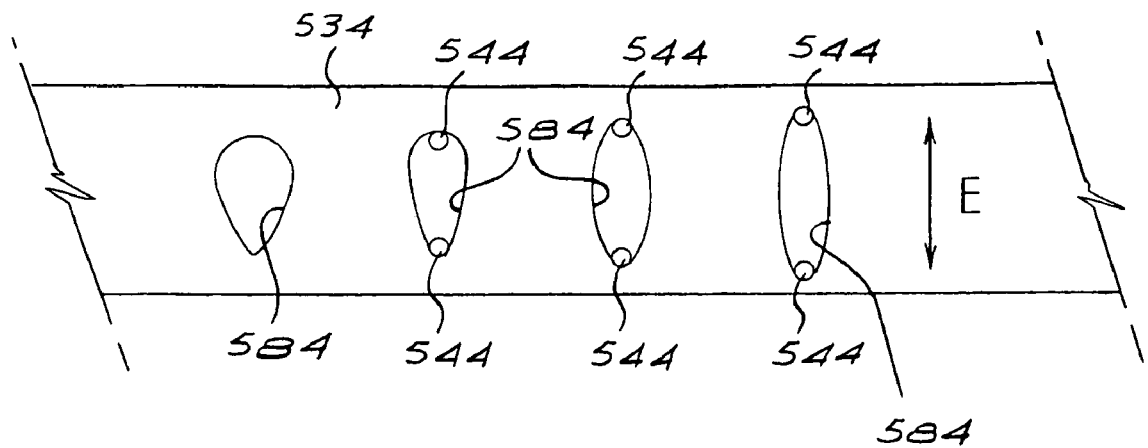
FIG. 15 is a top view of a component forming part of an apparatus for attaching leg elastics to a web according to yet another aspect of the invention.

FIG. 15 illustrates components forming part of an apparatus for deforming a moving web 534 in accordance with yet another aspect of the invention. The moving web in this case is similar to the web 434 described above, and also includes apertures 584 defining curved leg openings for adjacent outer covers. However, in the FIG. 15 arrangement, pairs of diverging pins 544 are arranged to penetrate the apertures 584 and then to diverge from one another so as to stretch the web 534 in a cross-machine direction, as indicated by the arrow "E", thereby to elongate the apertures 584 and reduce the curvatures of leg openings defined by these apertures.

The diverging pins 544 may be displaceable relative to the web 534 by various different carriers (not illustrated). For example, in one arrangement, the pins 544 may be mounted to a carrier movable along a track which runs in the machine direction, and which is contoured so as to raise and lower the carrier, thereby causing the pins 544 to penetrate the apertures 584 and to withdraw from these apertures, as required. In such an arrangement, the pins 544 may be laterally movable relative to the carrier, in a cross-machine direction, and guide rails may be provided for causing the pins to diverge so as to stretch the web 534, and to converge so as to restore the web to its initial condition.

In this way, as the web 534 engages the pins 544, it is stretched so that the curved leg openings defined by the apertures 584 elongate to facilitate the application of leg elastics (not illustrated) to the web, adjacent the apertures 584.

Instead of bonding an elastic strip to the web, the method of the invention could be used to bond strips formed from other materials to the web. Also, the method of the invention could be used to bond a folded-over edge portion of a web to an adjacent portion of the web next to a curved leg opening. Moreover, a combination of an elastic strip and a folded-over edge portion of a web may be used to provide elasticity about the opening.

Figure 16:
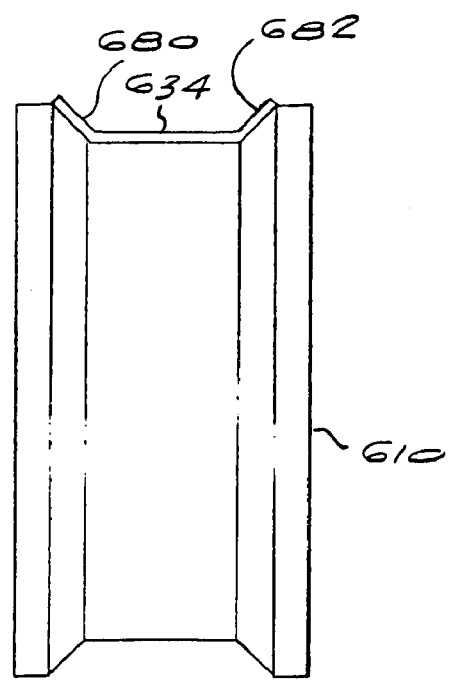
FIG. 16 is a cross-sectional view of a component forming part of an apparatus for attaching folded side edge regions of a web to adjacent regions of the web according to still another aspect of the invention.

FIG. 16 illustrates a component forming part of an apparatus for bonding folded-over portions of a web to adjacent portions thereof in accordance with yet a further aspect of the invention. In this arrangement, a grooved wheel 610 is used to fold side edge portions 680 and 682 of a moving web 634 out of the plane of the web, as shown. Tension in the web 634 or vacuum pressure can then be used to fold the side edge portions 680 and 682 onto adjacent portions of the web, next to curved leg openings (not visible).

The web 634 can then be stretched to reduce the degree of curvature of leg openings in the web, for example by inclined rollers (not shown) similar to the sets of rollers described above with reference to FIGS. 4 and 5 of the drawings, and the folded over strips can be bonded to the web 634, for example with an ultrasonic bonder (also not shown).

Although the invention has been described above with reference to the bonding of elastic strips or the like to a web for forming an outer cover for a training pant, it will be appreciated that the strips could also be bonded to a web for forming a bodyside liner for the garment. It will also be understood that the method is not limited to stretching as a means for deforming the web, and that the web could be deformed in various other ways, including twisting, turning or pivoting portions of the web relative to one another.

Having thus described the invention in detail, it should be apparent to those skilled in the art that various modifications can be made without departing from the scope of the invention as defined in the following claims.

What is claimed is:

1. A method for bonding surfaces on a web comprising:
   providing a web which includes leg openings and which defines at least a first bonding surface adjacent each leg opening, wherein the web defines a plane; and
   for each leg opening:
   deforming the web within the plane so as to modify the shape of the leg opening;
   providing a strip defining a second bonding surface;
   bonding together at least portions of the first and second bonding surfaces of the modified leg opening; and
   relaxing the web.

2. The method of claim 1, wherein providing the strip defining the second bonding surface comprises folding an edge region of the web during, before or after deformation of the web.

3. The method of claim 1, wherein providing the strip defining the second bonding surface comprises providing a strip of material separate from the web.

4. The method of claim 3, wherein the separate strip comprises an elastic material.

5. The method of claim 4, further comprising stretching the elastic material prior to bonding at least a portion of the first and second bonding surfaces.

6. The method of claim 4, wherein the elastic material comprises a composite elastic material.

7. The method of claim 3, further comprising curving the strip of material on at least one puck prior to bonding the strip of material to the web.

8. The method of claim 3, wherein the strip is cut prior to being bonded to the web.

9. The method of claim 1, wherein the web is stretchable, and deforming the web comprises stretching at least a portion of the web.

10. The method of claim 9, wherein the web is stretched in a machine direction.

11. The method of claim 9, wherein the web is stretched in a cross-machine direction.

12. The method of claim 9, wherein the web is stretched on a drum which includes projections.

13. The method of claim 9, wherein the web is stretched on a drum which includes recesses.

14. The method of claim 9, wherein the web is stretched on a drum which includes inclined surfaces.

15. The method of claim 1, wherein the web is deformed by rotating portions of the web.

16. The method of claim 1, wherein the web is deformed by turning portions of the web.

17. The method of claim 1, wherein the web is deformed by twisting portions of the web.

18. The method of claim 1, wherein the web defines curved leg openings, and deforming the web comprises modifying the curvature of each leg opening.

19. The method of claim 18, wherein deforming the web comprises reducing the degree of curvature of each leg opening.

20. The method of claim 18, wherein deforming the web comprises forming a straight or substantially straight edge from each curved leg opening.

21. The method of claim 1, wherein the web is deformed by means of diverging pins.

22. The method of claim 1, wherein the first and second bonding surfaces are bonded together by spaced-apart bonds.

23. The method of claim 1, wherein the first and second bonding surfaces are bonded together along at least one bonding line.

24. The method of claim 1, wherein the first and second bonding surfaces are bonded together by means of ultrasonic bonding.

25. The method of claim 1, wherein the first and second bonding surfaces are bonded together by means of thermal bonding.

26. The method of claim 1, wherein the first and second bonding surfaces are bonded together by means of pressure bonding.

27. The method of claim 1, wherein the web comprises a biaxially stretchable outer cover for an absorbent garment.

28. The method of claim 27, wherein the absorbent garment is a diaper, a training pant, an incontinence garment, or swim wear.

29. A method for bonding surfaces on a moving web comprising:
providing a web which includes curved leg openings and which defines at least a first bonding surface adjacent each leg opening; and
for each leg opening:
deforming the web so as to reduce the curvature of the leg opening;
providing a separate strip of material defining a second bonding surface;
bonding the second bonding surface on the separate strip of material to the first bonding surface on the web; and
relaxing the web.

30. A method for bonding surfaces on a moving web comprising:
providing a web travelling in a machine direction which includes curved leg openings and which defines at least a first bonding surface adjacent each leg opening; and,
for each leg opening:
deforming the web so as to modify the curvature of the leg opening;
folding an edge portion of the web to form a strip adjacent the leg opening before, during or after deformation of the web, the strip defining a second bonding surface;
bonding the second bonding surface on the folded strip to the first bonding surface on the web; and
relaxing the web.

31. The method of claim 30, including applying a strip of elastic material to the web prior to folding the edge portion of the web.

32. A method for making a disposable garment comprising:
providing an outer cover web;
forming a pair of opposed curved leg openings in the web, the leg openings defining at least a first bonding surface adjacent each leg opening; and
for each leg opening:
deforming the outer cover web so as to straighten the shape of the leg opening;
providing a strip defining a second bonding surface;
bonding together at least portions of the first and second bonding surfaces of the modified leg opening; and
relaxing the web.

33. A method for bonding surfaces on a web comprising:
providing a web which includes leg openings and which defines at least a first bonding surface adjacent each leg opening, wherein the web is stretchable; and
for each leg opening:
deforming the web including stretching at least a portion of the web so as to modify the shape of the leg opening;
providing a strip defining a second bonding surface;
bonding together at least portions of the first and second bonding surfaces of the modified leg opening; and
relaxing the web.

34. The method of claim 33, wherein the web is stretched in a machine direction.

35. The method of claim 33, wherein the web is stretched in a cross-machine direction.

36. The method of claim 33, wherein the web is stretched on a drum which includes projections.

37. The method of claim 33, wherein the web is stretched on a drum which includes recesses.

38. The method of claim 33, wherein the web is stretched on a drum which includes inclined surfaces.

* * * * *